(12) United States Patent
Suzuki et al.

(10) Patent No.: US 6,384,415 B1
(45) Date of Patent: May 7, 2002

(54) METHOD OF EVALUATING QUALITY OF SILICON WAFER AND METHOD OF RECLAIMING THE WATER

(75) Inventors: Tetsuo Suzuki, Kobe (JP); Kunio Otsuka, Hayward, CA (US)

(73) Assignees: Kabushiki Kaisha Kobe Seiko Sho (Kobe Steel, Ltd.), Kobe (JP); Kobe Precision Inc., Hayward, CA (US)

( * ) Notice: Subject to any disclaimer, the term of this patent is extended or adjusted under 35 U.S.C. 154(b) by 9 days.

(21) Appl. No.: 09/597,577

(22) Filed: Jun. 20, 2000

(51) Int. Cl.$^7$ ................................................ G01J 5/02
(52) U.S. Cl. .............................. 250/341.4; 250/341.5; 250/341
(58) Field of Search .......................... 250/341.4, 341.5

(56) References Cited

U.S. PATENT DOCUMENTS

| | | | | |
|---|---|---|---|---|
| 5,855,735 A | * | 1/1999 | Takada et al. | ............ 250/341.4 |
| 2001/0039101 A1 | * | 11/2001 | Wenski | .................... 250/341.4 |

FOREIGN PATENT DOCUMENTS

| | | |
|---|---|---|
| JP | 59-217673 | 12/1984 |
| JP | 6-3268 | 1/1994 |
| JP | 7-49305 | 2/1995 |
| JP | 9-17833 | 1/1997 |

OTHER PUBLICATIONS

Werner Kern, J. Electrochem. Soc., vol. 137, No. 6, pp. 1887–1892, "The Evolution of Silicon Wafer Cleaning Technology", Jun. 1990.

* cited by examiner

Primary Examiner—Scott J. Sugarman
Assistant Examiner—Mohammed Hasan
(74) Attorney, Agent, or Firm—Oblon, Spivak, McClelland, Maier & Neustadt, P.C.

(57) ABSTRACT

A method of evaluating the quality of a silicon wafer is characterized by analyzing a silicon wafer by an infrared absorption spectrum, and then evaluating the quality of the silicon crystal based on an absorbance ratio represented by the following formula (1):

$$\{(\text{Absorbance } \alpha_1 \text{ at an arbitrary wavenumber between 1055 and 1080 cm}^{-1}) - (\text{Absorbance } \alpha_{BL} \text{ of base line})\} / \{(\text{Absorbance } \alpha_2 \text{ at an arbitrary wavenumber between 1100 and 1120 cm}^{-1}) - (\text{Absorbance } \alpha_{BL} \text{ of base line})\} \quad (1)$$

wherein absorbances $\alpha_1$ and $\alpha_2$ represent absorbances of the measured silicon wafer, and base line absorbance $\alpha_{BL}$ represents the absorbance of a base line of the measured silicon wafer, which is drawn from 1030 to 1170 cm$^{-1}$. By using the quality evaluating method of the present invention, internal crystal defects of silicon can be precisely detected in a non-destructive manner. The method of the present invention thus has the advantages of improving productivity, decreasing reclaiming cost, etc.

6 Claims, 5 Drawing Sheets

METHOD OF EVALUATING QUALITY OF SILICON WAFER AND METHOD OF RECLAIMING THE WATER

BACKGROUND OF THE INVENTION

1. Field of the Invention

The present invention relates to a method of evaluating the quality of a silicon wafer, and a method of reclaiming the silicon wafer. By using the methods of the present invention, crystal defects present in the silicon wafer can be precisely be detected in a nondestructive manner. Therefore, the present invention is preferably used for evaluating the quality of a silicon wafer (a used silicon wafer) used in a process for manufacturing semiconductor devices, and reclaiming the silicon wafer.

2. Description of the Related Art

In the process for manufacturing semiconductor devices, a silicon wafer used as a test wafer or a monitor wafer is reused through polishing and cleaning after removal of various films (oxide films, and the like) formed on the surface thereof. Similarly, a silicon wafer for manufacturing devices, which becomes defective due to some abnormality in the process for manufacturing semiconductor devices is also reused as a test wafer or monitor wafer through film removal, polishing and cleaning. In the present invention, such a silicon wafer used for some purpose in the process for manufacturing devices is referred to as a "used silicon wafer". Among used silicon wafers, a silicon wafer reclaimed by any of various methods is referred to as a "reclaimed wafer".

The practical use of the reclaimed wafer has the great advantages of reducing the manufacturing cost of devices, and permitting effective use of resources. However, even the reclaimed wafer is required to have the same quality level as a new wafer with respect to surface defects, fine particle adhesion, surface metal concentration, etc. The quality of the reclaimed wafer is generally evaluated at the time the reclaiming process is completely finished, and only the reclaimed wafer whose quality agrees with a predetermined standard is reused. Therefore, various reclaiming methods have been proposed for providing high-quality reclaimed wafers at low cost.

The method of reclaiming the used silicon wafer generally comprises the step of removing films formed on the used silicon wafer, the step of polishing the wafer from which the films are removed, the step of cleaning the polished wafer, and the step of evaluating the quality of the final product. Particularly, various methods of providing excellent reclaimed wafers have been studied, in which the film removing step is improved.

In the film removing step, lapping, grinding, chemical etching, chemical-mechanical polishing, and the like are performed singly or in combination. In another method, the types of films formed on the wafer are determined by visual observation, surface resistance, infrared absorption spectra, light reflectance, or the like, and then the films are removed according to the characteristics of the films. For example, Japanese Unexamined Patent Publication No. 9-17833 discloses a method of reclaiming a used wafer in which the types of films formed on a wafer are estimated by infrared absorption spectra, and grouped into several patterns, and then reclaiming process is performed according to each of the patterns. This method has the advantage that even for a used semiconductor wafer having unknown history, the types of films formed on the wafer can easily be examined, and a film removing method suitable for each film can be used. However, this method comprises no evaluation of the internal quality of the wafer after removal of the films, and is thus difficult to obtain an excellent reclaimed wafer when crystal defects are present in the wafer.

On the other hand, for new wafers, particularly wafers produced by the Czochralski process which occupy most of the wafers currently used for semiconductors, an analytical method is carried out by using infrared absorption spectra for controlling the oxygen concentrations of wafers in a predetermined range. This is because supersaturated oxygen present in silicon is precipitated by heat treatment performed in a device process to cause the occurrence of fine crystal defects in a wafer. This method of measuring the oxygen concentration of a wafer using an infrared spectrum is defined in ASTM F1188-88 and ASTM F1189-88, and is generally used as a standard measurement method. For example, Japanese Unexamined Patent Publication No. 6-3268 discloses a method of measuring the concentrations of interstitial oxygen and substitutional carbon in a silicon wafer by infrared absorption spectroscopy; Japanese Unexamined Patent Publication No. 7-49305 discloses a method of rapidly and easily measuring a planar distribution of inter-stitial oxygen concentrations in a silicon single crystal by using infrared absorption of a silicon wafer which appears at 1107 $cm^{-1}$. Furthermore, in a process for producing semiconductor chips, an infrared analytical method is also used for evaluating an oxygen concentration and oxygen precipitates of a wafer.

In this way, the method of measuring an oxygen concentration of a new silicon wafer or effectively removing films formed on a used silicon wafer by using an infrared absorption spectrum is carried out. However, particularly for a used wafer, a method of evaluating the internal quality of a wafer after removal of films has not been proposed yet. However, in some used wafers, defects are induced in a wafer due to film deposition and heat treatment processes, or the crystal itself deteriorates to cause crystal defects, and thus the surface quality of the final product does not reach the required level due to these defects. In recent years, particularly, the surface quality level required for the reclaimed wafer has increased with increases in the degree of integration of a device, and thus the allowable number and size of crystal defects have been strictly limited, further increasing the above-described tendency. As a result, in present circumstances, not only a decrease in the inspection pass rate due to defects or abnormality in the reclaiming process, but also a decrease in the inspection pass rate based on the deterioration in internal quality of a wafer itself cannot be neglected.

SUMMARY OF THE INVENTION

The present invention has been achieved in consideration of the above-described situation. A first object of the present invention is to provide a method of evaluating the quality of a silicon wafer which is capable of precisely detecting internal crystal defects of a silicon wafer in a nondestructive manner.

A second object of the present invention is to provide a method of reclaiming a used silicon wafer which is capable of efficiently obtaining a high-quality reclaimed silicon wafer having no internal crystal defect.

In order to achieve the first object, a method of evaluating a silicon wafer of the present invention comprises analyzing a silicon wafer by an infrared absorption spectrum, and evaluating the quality of the silicon crystal based on an absorbance ratio represented by the following formula (1):

{(Absorbance α1 at an arbitrary wavenumber between 1055 and 1080 $cm^{-1}$)−(Absorbance αBL of base line)}/{(Absorbance α2 at an arbitrary wavenumber between 1100 and 1120 $cm^{-1}$)−(Absorbance αBL of base line)}     (1)

In the formula, absorbances α1 and α2 represent absorbances of the measured silicon wafer, and base line absorbance αBL represents the absorbance of a base line of the measured silicon wafer, which is drawn from 1030 to 1170 $cm^{-1}$.

In order to achieve the second object, a method of reclaiming a used silicon wafer of the present invention comprises the steps of removing films formed on a silicon wafer, and then evaluating the quality of the silicon crystal of the silicon wafer based on the above method.

DESCRIPTION OF THE PREFERRED EMBODIMENTS

The inventors intensively studied in order to provide a method of precisely detecting crystal defects in a silicon wafer in a non-destructive manner. As a result, it was found that the quality of the silicon crystal of a silicon wafer can be precisely evaluated by using an absorbance ratio in a specified wavenumber region in infrared absorption spectroscopy, leading to the achievement of the present invention.

The method of the present invention will be described in detail below based on the detailed experimental story leading to the achievement of the present invention.

The quality of a silicon wafer is generally evaluated by inspecting the number of LPD (Light Point Defects) by light scanning topography, with the exception of special application. In detail, LPD inspection comprises scanning a wafer surface by a laser beam to detect light scattered or irregularly reflected by particles, stains, flaws, bits, and the like present on the surface, and counting LPD. As a rule, LPD inspection is 100% inspection. The size of LPD is determined on the basis of the size of a polystyrene-latex sphere which provides equivalent scattering intensity. In most cases of LPD inspection, LPDs are measured at the same time as haze which correlates to surface micro roughness [refer to, for example, Jpn. J. Appl. Phys. Vol. 31, p721–728 (1992)].

Even by processing used silicon wafers by polishing and cleaning in the same batch, accepted products which show LPD numbers lower than a required level, and rejected products which show LPD numbers higher than the required level are mixed in LPD inspection of final products. This tendency is significantly observed in cases in which evaluation is made with the LPD lower detection limit strictly set to 0.20 μm or less. In consideration of the above situation, the inventors carried out studies for clarifying the cause of this phenomenon.

Figure 1:
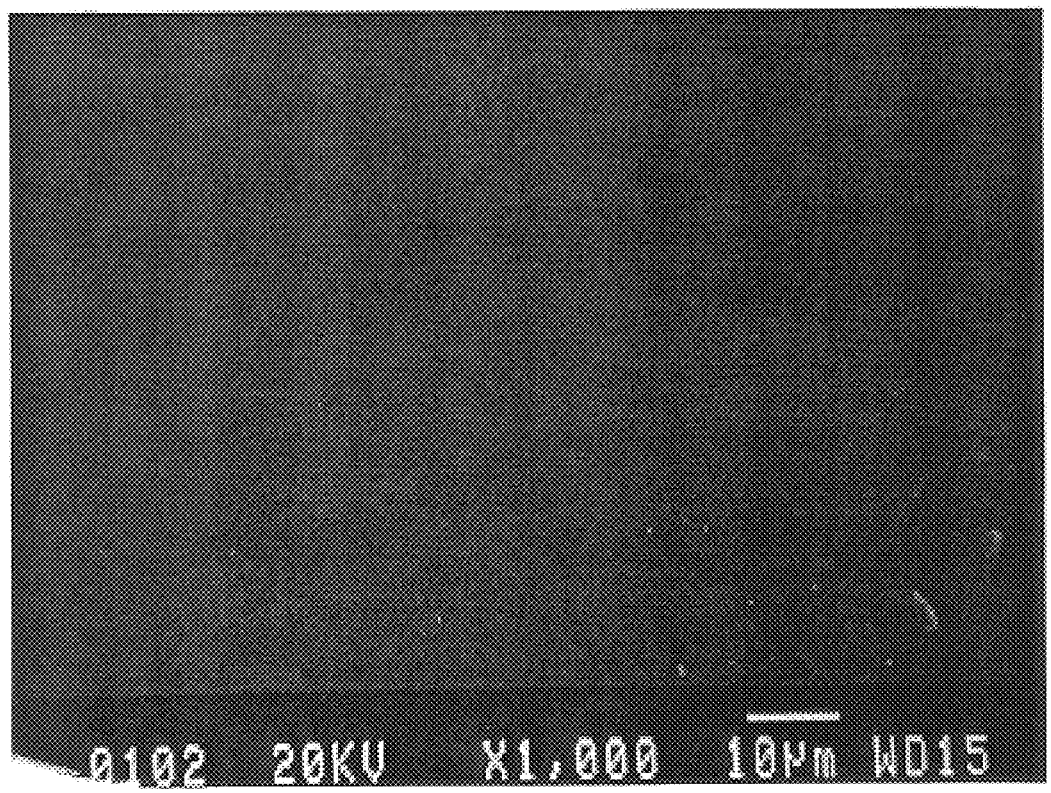
FIG. 1 is a scanning electron microscope photograph of wafer sample A having less crystal defect therein.
Figure 2:
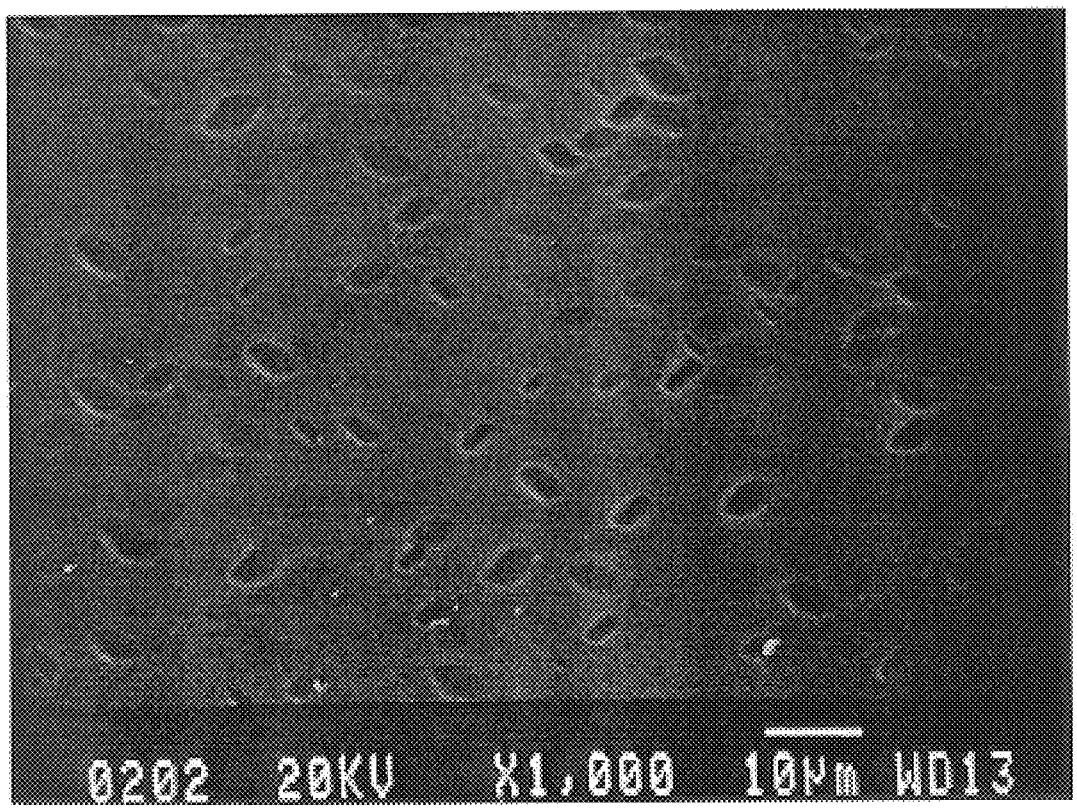
FIG. 2 is a scanning electron microscope photograph of wafer sample B having many crystal defects therein.

More specifically, a silicon wafer (sample A: a wafer having 30 LPD of 0.13 μm or more), which was decided as "accepted" by LPD inspection, and a silicon wafer (sample B: a wafer having 1931 LPD of 0.13 μm or more) which was decided as "rejected" were used, and each of the wafers was subjected to Wright etching, and then a fracture surface thereof was observed on a scanning electron microscope (SEM). FIGS. 1 and 2 are photographs of these samples. FIG. 1 is a SEM photograph of sample A having a small number of LPD, e.g., 30, and FIG. 2 is a SEM photograph of sample B having a large number of LPD, e.g., 1931. These photographs indicate that many crystal defects are present in the wafer of sample B in which many LPDs were detected.

Furthermore, as a result of analysis by Fourier transform infrared absorption spectroscopy (Fourier Transform Infrared; FTIR), it was found that the silicon wafer (sample B) having internal defects has a significant difference in a spectral absorption band at 1000 to 1200 $cm^{-1}$ from the normal silicon wafer (sample A).

Figure 3:
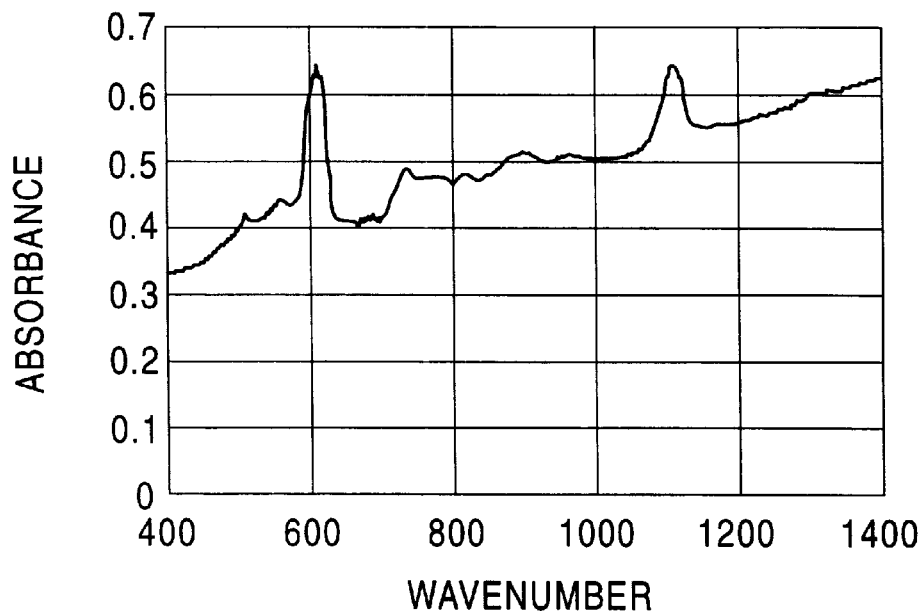
FIG. 3 is a graph showing a Fourier transform infrared absorption spectrum of the sample A.
Figure 4:
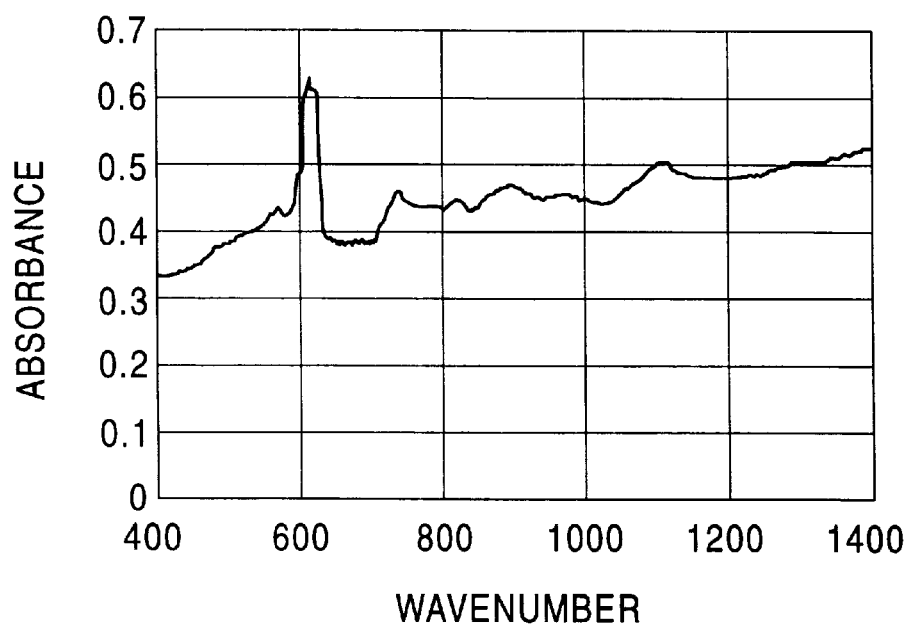
FIG. 4 is a graph showing a Fourier transform infrared absorption spectrum of the sample B.
Figure 5:
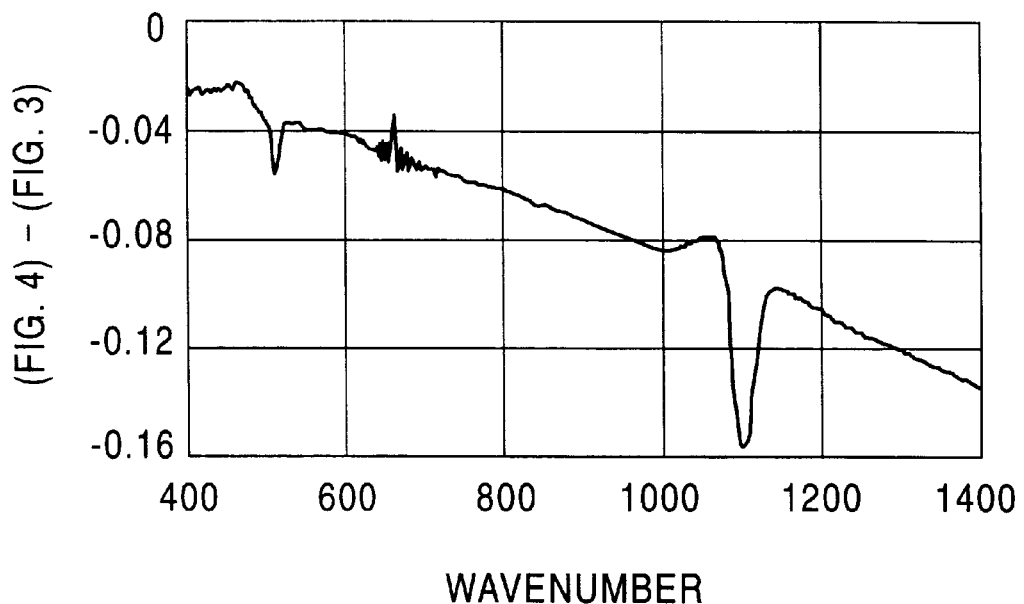
FIG. 5 is a graph showing the results obtained by subtracting the infrared spectrum shown in FIG. 3 from the infrared spectrum shown in FIG. 4.

FIGS. 3 and 4 are graphs showing the measurement results of FTIR spectra (wavenumber of 400 to 1400 $cm^{-1}$ of the samples A and B, respectively. Comparison between these graphs reveals that the normal wafer (sample A) having less LPD shows a characteristic absorption band showing maximum absorption at 1106 $cm^{-1}$, while the sample B having many LPDs shows weak absorption intensity at 1106 $cm^{-1}$, and the tendency that the absorption band broadens on the low-wavenumber side. Such a difference between the infrared absorption spectra of both samples is further clarified by referring to FIG. 5 [a graph showing the results obtained by subtracting the spectrum (FIG. 3) of sample A from the spectrum (FIG. 4) of sample B]. Referring to FIG. 5, a minimum (1106 $cm^{-1}$) and a maximum (1066 $cm^{-1}$) are observed near 1000 to 1200 $cm^{-1}$. This shows a significant difference between the FTIR spectral patterns of the samples A and B.

In the absorption spectra shown in FIGS. 3 to 5, a maximum absorption peak at 1106 $cm^{-1}$ is due to inter-stitial oxygen atoms present in the silicon wafer. It has already been known that the inter-stitial oxygen atoms are precipitated or re-dissolved in the process for heat-treating a wafer to cause micro defects in the silicon crystal. For example, in Appl. Phys. Lett., Vol. 35, No. 5, p483–487 (1980) or Appl. Phys. Lett., Vol. 38, No. 11, p867–870 (1981), it is reported that precipitation of inter-stitial oxygen forms nuclei to decrease the absorption intensity at 1106 $cm^{-1}$ and, at the same time, cause absorption at near 1225 $cm^{-1}$ due the nuclei. However, as a result of research conducted by the inventors, a wafer having many LPD showed a decrease in the absorption intensity at 1106 $cm^{-1}$, but new absorption at near 1225 $cm^{-1}$, which is reported in the above publications, was little detected. It was rather found that a wafer having many internal defects has a characteristic absorption band at near 1100 $cm^{-1}$, which is different from a wafer having no internal defect, as shown in FIG. 4.

On the basis of the above results, the inventors repeated further studies as to whether the characteristic absorption band can be digitized as an index which represents the internal crystal defects of a wafer. As a result, it was found that by using as an index an absorbance ratio represented by the formula (1), the quality of a silicon crystal can precisely be evaluated.

{(Absorbance α1 at an arbitrary wavenumber between 1055 and 1080 cm$^{-1}$)-(Absorbance αBL of base line)}/{(Absorbance α2 at an arbitrary wavenumber between 1100 and 1120 cm$^{-1}$)-(Absorbance αBL of base line)} (1)

In the formula, absorbances α1 and α2 represent absorbances of the measured silicon wafer, and base line absorbance αBL represents the absorbance of a base line of the measured silicon wafer, which is drawn from 1030 to 1170 cm$^{-1}$.

Namely, the present invention is characterized by using, as an index which indicates the internal crystal defects of a wafer, the ratio (A/B) of absorbance A obtained by (absorbance α1 at an arbitrary wavenumber between 1055 and 1080 cm$^{-1}$)-(absorbance αBL of base line) to absorbance B obtained by (absorbance α2 at an arbitrary wavenumber between 1100 and 1120 cm$^{-1}$)-(absorbance αBL of base line). The idea of evaluating the internal quality of a wafer by using this index is not known yet, and is thus novel.

Japanese Examined Patent Publication No. 4-49904 discloses a method in which the peak heights of infrared absorption spectra of a silicon semiconductor, which are observed at 1150 to 1050 cm$^{-1}$ and 530 to 500 cm$^{-1}$, are read so that a density of micro defects produced in the process for manufacturing silicon semiconductor devices is detected in the stage of a substrate wafer before the process by using a ratio of the absorption coefficients as an index. This method is similar to the present invention with respect to detection means for detecting internal crystal defects of silicon by using a ratio of the absorption coefficients at specified two wavelengths as an index, but is completely different from the present invention in the measurement criterion. Namely, in this method, the ratio of the absorption coefficient at a wavelength (long wavelength side) near 1106 cm$^{-1}$, which is known as a characteristic absorption of inter-stitial oxygen, to the absorption coefficient at 530 to 500 cm$^{-1}$, which is considered as a characteristic absorption of substitutional oxygen, is used as the evaluation criterion for wafer quality. However, in the present invention, the ratio of absorbance A at a wavenumber of (1055 to 1080 cm$^{-1}$) to absorbance B at a wavenumber (1100 to 1120 cm$^{-1}$) in the shape of a characteristic absorption band at near 1100 cm$^{-1}$ is used as the evaluation criterion for wafer quality, and thus the reference wavelength regions of both methods are different. Therefore, the most important point of the present invention lies in that a characteristic absorption band at near 1100 cm$^{-1}$ is observed in a wafer having internal crystal defects, which is not observed in a wafer having no internal defect, as shown in FIG. 4. This is satisfactorily digitized as the evaluation criterion for quality to specify the formula (1), resulting in the achievement of the present invention. This technical idea is neither disclosed nor suggested in the above publications.

Preferably, it is recommended to evaluate the quality of a silicon crystal on the basis of the absorbance ratio represented by the following formula (2).

{(Average absorbance α1 at 1055 to 1080 cm$^{-1}$)-(Absorbance αBL of base line)}/{(Maximum absorbance α2' at 1100 to 1120 cm$^{-1}$)-(Absorbance αBL of base line)} (2)

In the formula, absorbances α1' and α2' represent absorbances of the measured silicon wafer, and base line absorbance represents the same as the above.

The formula (2) uses (average absorbance α1 at 1055 to 1080 cm$^{-1}$) in place of α1, and (maximum absorbance α2' at 1102 to 1115 cm$^{-1}$) in place of α2. The use of these indexes further improves the precision of quality evaluation.

The method more preferably comprises evaluating the quality of a silicon wafer by deciding that a silicon crystal has good quality when the absorbance ratio represented by the following formula (3) is 0.20 or less (more preferably 0.15 or less).

{(Absorbance α1" at 1066 cm$^{-1}$)-(Absorbance αBL of base line)}/{(Absorbance α2" at 1106 cm$^{-1}$)-(Absorbance αBL of base line)} (3)

In the formula, absorbances α1" and α2" represent absorbances of the measured silicon wafer, and base line absorbance represents the same as the above.

The formula (3) uses specified absorbance α1" at 1066 cm$^{-1}$ in place of α1 in the formula (1), and specified absorbance α2" at 1106 cm$^{-1}$ in place of α2 in the formula (1). The use of these indexes permits the evaluation of internal crystal defects of a wafer with very high precision.

As described above, the present invention is characterized by using the absorbance ratio represented by each of the formulae (1) to (3) as the evaluation criterion for internal quality of a wafer. However, in analyzing a silicon wafer to be measured by an infrared absorption spectrum, particularly analyzing a used silicon wafer, the films formed on the silicon wafer are previously removed. In this stage, it is basically sufficient that the films are moved to an extent which permits infrared absorption analysis, and the films need not be completely removed. Of course, it is preferable to completely remove the films.

As the removal method, known removal methods such as lapping, grinding, chemical etching, chemical-mechanical polishing, and the like may be used singly or in combination. The removal method is not limited, and the films are preferably removed under conditions appropriately selected from ordinary conditions for removing films of a wafer.

Next, the internal crystal defects of the silicon wafer from which the films are removed as described above are detected by an infrared absorption spectrum (measurement range 400 to 4000 cm$^{-1}$, spectral indication; absorbance) of a central portion thereof. The measurement conditions for an infrared absorption spectrum are appropriately selected from ordinary infrared analysis conditions for detecting the oxygen concentration of a wafer. For example, the measurement under conditions in the following ranges is recommended.

Resolution: 0.5 to 4 cm$^{-1}$

Number of times of integration: 25 to 250 times

Detector: TGS (Triglycine Sulfate)

The wafer subjected to infrared analysis as described above is then passed through each of the polishing and cleaning steps, followed by quality evaluation of a final product.

As the polishing method, polishing means ordinarily used for the method of reclaiming a silicon wafer can be appropriately selected. For example, rough polishing is performed by a one-side polishing machine to which a rigid polyurethane nonwoven fabric pad is attached, using a commercial polishing solution under a polishing pressure of 350 to 450 g/cm$^2$. Secondary polishing is performed by the one-side polishing machine to which a nonwoven fabric pad having hardness slightly lower than the pad for rough polishing is attached, under a polishing pressure of 200 to 300 g/cm$^2$. Finish polishing is performed by the one-side polishing machine to which a soft foamed polyurethane pad is attached, using a commercial finish polishing solution under a polishing pressure of 100 to 150 g/cm$^2$.

Also, cleaning after polishing is not limited, and an ordinary RCA cleaning method can be used. The RCA cleaning method is a silicon wafer cleaning method reported by RCA in 1970, and uses a mixture of an alkali, an acid and hydrogen peroxide. Cleaning methods based on this idea are referred to as "RCA Standard Clean", and many improvements of the cleaning method have been reported. Details of the method are described in, for example, J. Electrochemical Society, Vol. 137, No. 6, p1887–1892 by Werner Kern who is a developer of the RCA cleaning method. More specifically, adhered fine particles and organic materials are first removed by using a mixture of ammonium hydroxide and hydrogen peroxide, and then surface oxide films are removed by diluted hydrofluoric acid. Finally, in order to remove metal impurities, cleaning is performed with a mixture of hydrochloric acid and hydrogen peroxide.

Then, the final wafer product after cleaning is subjected to quality evaluation. As the evaluation method, the above-described LPD inspection is recommended.

Although the method of reclaiming a silicon wafer by using the evaluation criterion for quality of the present invention has been described above, the method of calculating the absorbance ratio of the formula (1), which is the most important point of the present invention, will be described in detail below with reference to an example. In the described below, used test wafers of Ø200 mm having various films are given as typical examples, and described in detail. However, the wafers are not limited to these examples, and of course, the method of the present invention can be applied to not only used silicon wafers but also new silicon wafers.

The used test wafer was etched with an etching solution comprising hydrofluoric acid as a main component to partially remove oxide films, nitride films, and metal films formed on the wafer. Then, lapping was performed for removing the films remaining after etching and a discolored layer, and adhered contaminants formed by etching. Furthermore, in order to remove a damaged layer newly formed by lapping, etching was performed with a potassium hydroxide aqueous solution. In the series of processing, the films present on the surface of the wafer were completely removed.

Next, the internal crystal defects of the silicon wafer from which the films were removed as described above were detected by an infrared absorption spectrum (measurement range 400 to 4000 $cm^{-1}$) of a central portion thereof. The measurement conditions of the infrared absorption spectrum were as follows.

Resolution: 2 $cm^{-1}$
Number of times of integration: 50 times
Detector: TGS (Triglycine Sulfate)

Figure 6:
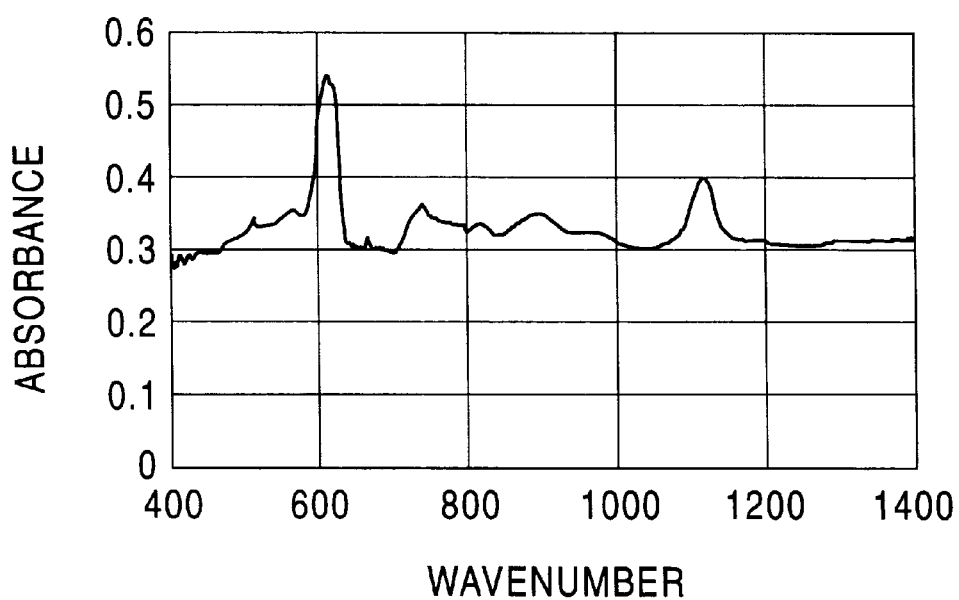
FIG. 6 is a graph showing an infrared absorption spectrum of a measured wafer at 400 to 1400 $cm^{-1}$.
Figure 7:
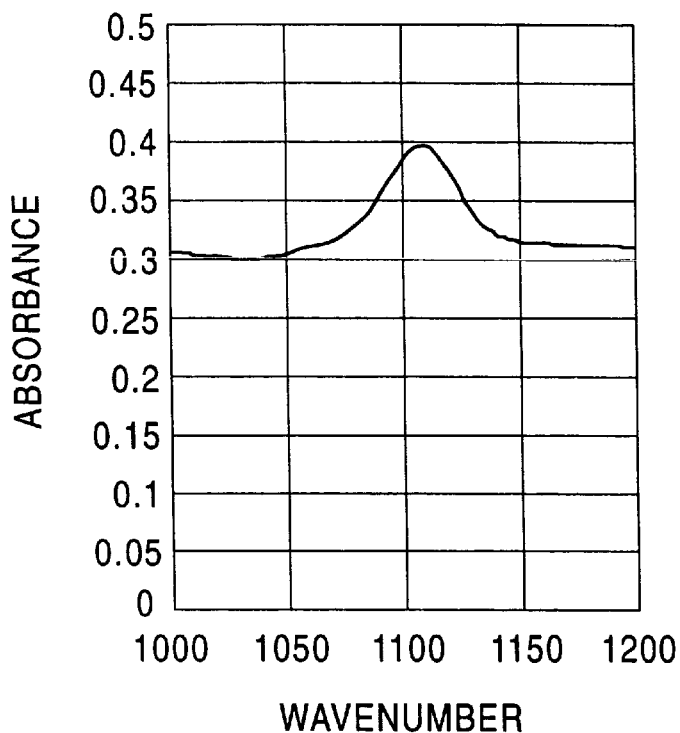
FIG. 7 is an enlarged graph showing the infrared spectrum at 1000 to 1200 $cm^{-1}$ shown in FIG. 6.

FIG. 6 shows the results of an infrared absorption spectrum at 400 to 4000 $cm^{-1}$ which was measured as described above. FIG. 7 is an enlarged graph showing the infrared absorption spectrum at 1000 to 1200 $cm^{-1}$ shown in FIG. 6. FIG. 7 indicates that characteristic absorption having a maximum peak at near 1106 $cm^{-1}$ is present.

In FIG. 7, a base line is determined. Although the base line is determined by using both bases of the spectrum pattern shown in FIG. 7, the base line is drawn from 1030 $cm^{-1}$ to 1170 $cm^{-1}$ in FIG. 7.

Figure 8:
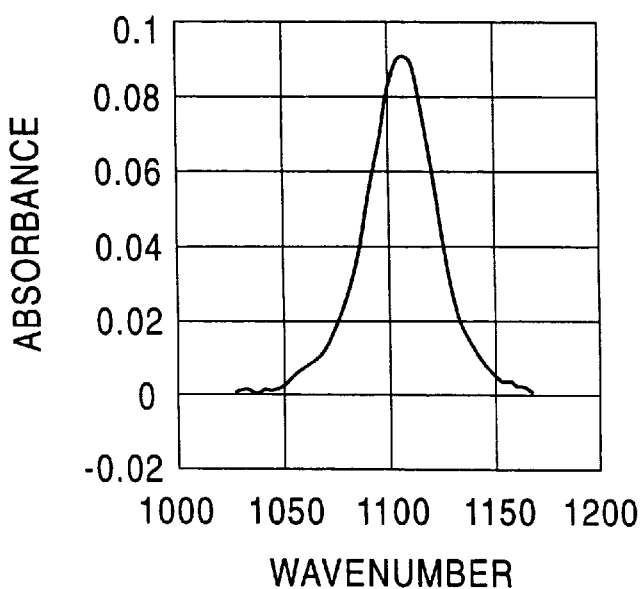
FIG. 8 is a graph showing the results obtained by subtracting the spectrum of a base line from 1030 to 1170 $cm^{-1}$ from the infrared absorption spectrum shown in FIG. 7.

FIG. 8 is a graph showing the results obtained by subtracting the spectrum of the base line from the infrared absorption spectrum of FIG. 7. On the basis of the thus-obtained spectrum, the absorbance ratio represented by each of the formulae (1) to (3) is calculated. Particularly, in use of the absorbance ratio of the formula (3) as the evaluation criterion for quality, a wafer showing an absorbance ratio of 0.2 or less, preferably 0.15 or less, can be decided as "accepted product" having no internal crystal defect.

The surface of the wafer subjected to infrared analysis as described above was polished by an ordinary method using a polishing solution comprising alkaline colloidal silica as a main component. Polishing was carried out in tree steps of rough polishing, secondary polishing and finish polishing by using one-side polishing machine SPAW50 produced by SpeedFam. As the polishing pad and polishing solution, SUBA600 produced by Rodel and Nalco 2360 for rough polishing, SUBA400 produced by Rodel and Nalco 2360 for secondary polishing, and UR100 produced by Rodel and FGL3900 produced by Fujimi for finish polishing were respectively used.

Next, the wafer after polishing was RCA-cleaned by using a multi-bath cleaning apparatus. As the cleaning solution, a mixture (SC1) of ammonium hydroxide and hydrogen peroxide, diluted hydrofluoric acid (DHF), and a mixture (SC2) of hydrochloric acid and hydrogen peroxide were successively used. After cleaning, LPD measurement was carried out by using Surfscan 6220 produced by Tencor Co., Ltd.

Table 1 shows the results of the absorbance ratios calculated on the basis of the formula (3), LPD obtained by LPD inspection, and haze with respect to the wafers (Nos. 1 to 12) measured in this example. As a reference example, new wafers (Reference Examples 1 and 2) used as used wafers were processed by the same method as the above. The results are also shown in Table 1. As shown in Table 1, LPD was classified into sizes of 0.13 to 0.16 $\mu m$, 0.16 to 0.20 $\mu m$, 0.20 to 0.50 $\mu m$, and 0.50 $\mu m$ or more in terms of polystyrene latex. In Table 1, haze of each sample is shown by a relative value assuming that the value of Reference Example 1 is 1.00.

TABLE 1

| Wafer ID | α(1066)/α(1106) | Light Point Defects* | | | | Total | Haze** |
|---|---|---|---|---|---|---|---|
| | | 0.13–0.16 | 0.16–0.20 | 0.20–0.50 | 0.50 or more | | |
| #1 | 0.072 | 31 | 8 | 4 | 1 | 44 | 1.05 |
| #2 | 0.066 | 21 | 3 | 2 | 2 | 28 | 0.98 |
| #3 | 0.325 | 1444 | 475 | 22 | 5 | 1946 | 3.55 |
| #4 | 0.245 | 1192 | 294 | 11 | 2 | 1499 | 3.28 |
| #5 | 0.059 | 48 | 10 | 3 | 2 | 63 | 1.01 |
| #6 | 0.056 | 15 | 10 | 1 | 0 | 26 | 1.06 |
| #7 | 0.211 | 722 | 243 | 10 | 1 | 976 | 2.40 |

TABLE 1-continued

Absorbance ratio, LPD and Haze

| Wafer ID | α(1066)/ α(1106) | Light Point Defects* | | | | Total | Haze** |
|---|---|---|---|---|---|---|---|
| | | 0.13–0.16 | 0.16–0.20 | 0.20–0.50 | 0.50 or more | | |
| #8 | 0.171 | 286 | 87 | 15 | 8 | 396 | 1.53 |
| #9 | 0.091 | 40 | 3 | 0 | 2 | 45 | 0.99 |
| #10 | 0.079 | 19 | 8 | 2 | 0 | 29 | 1.00 |
| #11 | 0.067 | 50 | 7 | 1 | 0 | 58 | 1.05 |
| #12 | 0.269 | 19319 | 8093 | 1104 | 45 | 28561 | 3.48 |
| #13 | 0.251 | 29825 | 133 | 10 | 4 | 29972 | 4.00 |
| #14 | 0.086 | 28 | 2 | 0 | 1 | 31 | 1.12 |
| 1*** | 0.052 | 7 | 4 | 2 | 0 | 13 | 1.00 |
| 2*** | 0.065 | 10 | 2 | 2 | 1 | 15 | 0.99 |

*Light Point Defects were classified into sizes of 0.13 to 0.16 μm, 0.16 to 0.20 μm, 0.20 to 0.50 μm and 0.50 μm or more in terms of polystyrene latex.
**Haze was shown by a relative value assuming that the value of Reference Example 1 is 1.00.
***Reference Example Table 1 indicates that a wafer showing an absorbance ratio of the formula (3) of 0.20 or less, particularly 0.15 or less, exhibits substantially the same degrees of LPD and Haze as Reference Examples 1 and 2, and a reclaimed test wafer having good characteristics is obtained. On the other hand, a wafer showing an absorbance ratio of the formula (3) of over 0.20 exhibits Haze of not less than 2 times as high as the reference examples, and LPD of not less than ten times as high as the reference examples.

The present invention can provides a method of evaluating the quality of a silicon wafer which is capable of precisely detecting internal crystal defects thereof in a non-destructive manner, and a method of reclaiming a used silicon wafer which is capable of efficiently obtaining a high-quality reclaimed wafer having no internal crystal defect. The present invention can precisely detect internal crystal defects of silicon in a non-destructive manner so that only good products having no internal defect can be transferred to each of the polishing, cleaning and final inspection without causing the problem of a conventional method in that defective products are present in the stage of quality evaluation of final products. Therefore, the present invention has the industrial advantages of improving productivity, decreasing the reclaiming cost, etc.

What is claimed is:

1. A method of evaluating the quality of a silicon wafer comprising analyzing a silicon wafer by an infrared absorption spectrum, and then evaluating the quality of the silicon crystal based on an absorbance ratio represented by the following formula (1):

$$\{(\text{Absorbance } \alpha1 \text{ at an arbitrary wavenumber between } 1055 \text{ and } 1080 \text{ cm}^{-1})-(\text{Absorbance } \alpha BL \text{ of base line})\}/\{(\text{Absorbance } \alpha2 \text{ at an arbitrary wavenumber between } 1100 \text{ and } 1120 \text{ cm}^{-1})-(\text{Absorbance } \alpha BL \text{ of base line})\} \quad (1)$$

wherein absorbances $\alpha1$ and $\alpha2$ represent absorbances of the measured silicon wafer, and base line absorbance $\alpha BL$ represents the absorbance of a base line of the measured silicon wafer, which is drawn from 1030 to 1170 cm$^{-1}$.

2. A method of evaluating the quality of a silicon wafer according to claim 1, comprising analyzing a silicon wafer by an infrared absorption spectrum, and then evaluating the quality of the silicon crystal as good when an absorbance ratio represented by the following formula (3) is 0.20 or less:

$$\{(\text{Absorbance } \alpha1" \text{ at } 1066 \text{ cm}^{-1})-(\text{Absorbance } \alpha BL \text{ of base line})\}/\{(\text{Absorbance } \alpha2" \text{ at } 1106 \text{ cm}^{-1})-(\text{Absorbance } \alpha BL \text{ of base line})\} \quad (3)$$

wherein absorbances $\alpha1"$ and $\alpha2'$ represent absorbances of the measured silicon wafer, and base line absorbance $\alpha BL$ represents the absorbance of a base line of the measured silicon wafer, which is drawn from 1030 to 1170 cm$^{-1}$.

3. A method of evaluating the quality of a silicon wafer according to claim 1, comprising analyzing a silicon wafer by an infrared absorption spectrum, and then evaluating the quality of the silicon crystal as good when an absorbance ratio represented by the following formula (3) is 0.15 or less:

$$\{(\text{Absorbance } \alpha1" \text{ at } 1066 \text{ cm}^{-1})-(\text{Absorbance } \alpha BL \text{ of base line})\}/\{(\text{Absorbance } \alpha2" \text{ at } 1106 \text{ cm}^{-1})-(\text{Absorbance } \alpha BL \text{ of base line})\} \quad (3)$$

wherein absorbances $\alpha1"$ and $\alpha2"$ represent absorbances of the measured silicon wafer, and base line absorbance $\alpha BL$ represents the absorbance of a base line of the measured silicon wafer, which is drawn from 1030 to 1170 cm$^{-1}$.

4. A method of evaluating quality according to claim 1, using a used silicon wafer.

5. A method of reclaiming a used silicon wafer comprising the steps of:
    removing films formed on a silicon wafer; and
    evaluating the equality of the silicon crystal of the silicon wafer based on a method according to claim 1.

6. A method of evaluating the quality of a silicon wafer comprising analyzing a silicon wafer by an infrared absorption spectrum, and then evaluating the quality of the silicon crystal based on an absorbance, ratio represented by the following formula (2):

$$\{(\text{Average absorbance } \alpha1' \text{ at } 1055 \text{ to } 1080 \text{ cm}^{-1})-(\text{Absorbance } \alpha BL \text{ of base line})\}/\{(\text{Maximum absorbance } \alpha2' \text{ at } 1100 \text{ to } 1120 \text{ cm}^{-1})-(\text{Absorbance } \alpha BL \text{ of base line})\} \quad (2)$$

wherein absorbances $\alpha1'$ and $\alpha2'$ represent absorbances of the measured silicon wafer, and base line absorbance $\alpha BL$ represents the absorbance of a base line of the measured silicon wafer, which is drawn from 1030 to 1170 cm$^{-1}$.

* * * * *

UNITED STATES PATENT AND TRADEMARK OFFICE
CERTIFICATE OF CORRECTION

PATENT NO. : 6,384,415 B1
DATED : May 7, 2002
INVENTOR(S) : Suzuki et al.

It is certified that error appears in the above-identified patent and that said Letters Patent is hereby corrected as shown below:

<u>Title page, Item [54] and column 1, lines 1-3,</u>
Delete title in its entirety and replace with
-- (54) METHOD OF EVALUATING QUALITY OF SILICON WAFER AND METHOD OF RECLAIMING THE WAFER --.

Signed and Sealed this

Eleventh Day of February, 2003

JAMES E. ROGAN
*Director of the United States Patent and Trademark Office*